(12) United States Patent
Shechter

(10) Patent No.: US 7,020,236 B2
(45) Date of Patent: Mar. 28, 2006

(54) CONE BEAM CT SCANNERS WITH REDUCED SCAN LENGTH

(75) Inventor: Gilad Shechter, Haifa (IL)

(73) Assignee: Koninklijke Philips Electronics N.V., Eindhoven (NL)

(*) Notice: Subject to any disclaimer, the term of this patent is extended or adjusted under 35 U.S.C. 154(b) by 97 days.

(21) Appl. No.: 10/363,894

(22) PCT Filed: May 6, 2002

(86) PCT No.: PCT/IL02/00354

§ 371 (c)(1),
(2), (4) Date: Dec. 5, 2003

(87) PCT Pub. No.: WO03/092502

PCT Pub. Date: Nov. 13, 2003

(65) Prior Publication Data

US 2004/0071257 A1    Apr. 15, 2004

(51) Int. Cl.
*A61B 6/03* (2006.01)
*A61B 6/04* (2006.01)

(52) U.S. Cl. .............. 378/17; 378/15; 378/20; 378/196

(58) Field of Classification Search ............. 378/4, 378/15, 17, 19, 196, 197, 20
See application file for complete search history.

(56) References Cited

U.S. PATENT DOCUMENTS

| | | | |
|---|---|---|---|
| 4,989,142 A | 1/1991 | Crawford | 382/131 |
| 5,802,134 A | 9/1998 | Larson et al. | 378/4 |
| 5,881,122 A * | 3/1999 | Crawford et al. | 378/4 |
| 5,999,587 A * | 12/1999 | Ning et al. | 378/4 |
| 6,229,869 B1 * | 5/2001 | Hu | 378/4 |
| 6,324,246 B1 * | 11/2001 | Ruimi | 378/15 |
| 6,400,791 B1 * | 6/2002 | Schwarz | 378/17 |
| 6,415,012 B1 * | 7/2002 | Taguchi et al. | 378/15 |
| 6,580,777 B1 * | 6/2003 | Ueki et al. | 378/17 |
| 6,658,081 B1 * | 12/2003 | Bruder et al. | 378/15 |
| 6,751,283 B1 * | 6/2004 | van de Haar | 378/17 |
| 2002/0141628 A1 * | 10/2002 | Bruder et al. | 382/131 |

FOREIGN PATENT DOCUMENTS

| | | |
|---|---|---|
| DE | 199 28 738 | 1/2001 |
| EP | 0 981 996 | 3/2000 |

(Continued)

OTHER PUBLICATIONS

Grass, M. et al.; "3D Cone-Beam CT Reconstruction for Circular Trajectories;"(2000;) Phys. Med. Biol.; vol. 45; pp. 329-347.

(Continued)

*Primary Examiner*—Allen C. Ho
(74) *Attorney, Agent, or Firm*—Thomas M. Lundin

(57) ABSTRACT

Computerized tomography apparatus for reconstructing attenuation values within a volume comprising: an x-ray source situated operative to rotate about said volume, in a rotation plane, while irradiating at least a portion of the volume; a plurality of rows of x-ray detectors illuminated by said rotating x-ray source situated on an opposite side of the volume; a patient support operative to move a patient through a space between the source and detectors at an angle to the normal to the rotation plane, while the x-ray source illuminates the detectors; and a controller operative to compute the angle based on at least one of a radius R of said rotation, a radius r of said volume and a helix pitch, m, defined as a distance the patient support moves during a single rotation of the x-ray source.

12 Claims, 4 Drawing Sheets

FOREIGN PATENT DOCUMENTS

WO      WO 99/01736      1/1999

OTHER PUBLICATIONS

Kachelriess, M. et al.; "Advanced Single-Slice Rebinning in Cone-Beam Spiral CT;" Apr. 2000; Med. Phys.; vol. 27, No. 4; pp. 754-772.

Kudo, H. et al.; "Quasi-Exact Filtered Backprojection Algorithm for Long-Object Problem in Helical Cone-Beam Tomography;" Sep. 2000; IEEE Transactionson Medical Imaging; vol. 19, No. 9; pp. 902-921.

Schaller, S. et al.; "Exact Radon Rebinning Algorithm for the Long Object Problem in Helical Cone-Beam CT;" May 2000; IEEE Transactionson Medical Imaging; vol. 19, No. 5; pp. 361-375.

Wang, G. et al.; "A General Cone-Beam Reconstruction Algorithm;" Sep. 1993; IEEE Transactionson Medical Imaging; vol. 12, No. 3; pp. 486-496.

\* cited by examiner

CONE BEAM CT SCANNERS WITH REDUCED SCAN LENGTH

FIELD OF THE INVENTION

The invention relates to CT helical scanners utilizing a cone beam source.

BACKGROUND OF THE INVENTION

An important criterion in the performance of computed tomography (CT) is the ability to image a large volume in a short time period. This allows for reduced artifacts caused by patient movement and for higher patient throughput.

One method of improving throughput is to utilize a helical scan. In such a scan, an x-ray source that irradiates a patient rotates about the patient in a helical trajectory. Attenuation data is acquired along the entire trajectory. This data is used to reconstruct "slices" of cross-sectional attenuation images perpendicular to the axis of the helix.

Another method, sometimes used in conjunction with the helix scan, provides a plurality of axially displaced rows of circumferentially spaced detectors. Scanners embodying this method are sometimes called "multi-slice" scanners. Generally, a single source is used to irradiate the patient (and the multiple slices within the patient), such that the patient is irradiated by a "cone beam". At least some of the detectors detect attenuation data that does not represent attenuation through a slice perpendicular to the axis. Since the standard reconstruction algorithms for CT are based on axial slices, multi-slice methods intrinsically utilize inconsistent data in reconstructing the slices transverse to the axis. However, so long as the angle of the radiation is relatively low, this effect can be neglected without causing substantial artifacts. As the angle of the cone beam increases, so do artifacts. Generally, special cone beam reconstruction algorithms are used when the angle is great enough to cause bothersome artifacts.

Cone beam reconstruction algorithms have been developed which take account of the non-transverse nature of the data traces. Representative examples of such algorithms are taught in "A General Cone-Beam Reconstruction Algorithm" by Ge Wang, et al. IEEE Trans. Med. Imag. Vol. 12, No. 3, September 1993, Pages 486–496 and "Advanced single-slice rebinning in cone-beam spiral CT" by Marc Kachelrieβ, et al, Med. Phys. Vol. 27, No. 4, April 2000, pages 754–772.

One of the features of reconstructing attenuation maps from cone beam (as well as other helical) acquisition methods is that the length of the helix described by the x-ray source is larger than the length of the region being scanned. This additional length is required since, in order to obtain full coverage of the length required, some of the non-transverse rays at the beginning and end of the scan are not usable.

There exist methods of reducing the length of said scans. WO 99/01736 describes a method in which the helix axis and the patient axis are coincident and the plane formed by the axis of the central row of detectors and the X-ray source is tilted with respect to the joint patient/helix axis. This is said to improve the efficiency of use of the detector array.

In general, shortening of the helical path results in the generation of artifacts originating from the conical geometry of the beams. Shortening of the helical path can not go beyond a limit determined by the conical reconstruction method without causing additional artifacts.

U.S. Pat. No. 4,989,142 and EP patent publication EP 0 981 996 describe methods for converting data in systems in which the patient and helix axis are different to transaxial patient data.

In some CT scanners, the axis of the patient (i.e., the axis along which the bed carrying the patient moves, during the scan) can be angled with respect to the axis of rotation of the CT scanner and the acquired "axial" slices (which are transaxial with respect to the helix axis). As used herein, unless otherwise specified, the term "axis" or "axial" refers to the axis of rotation of the CT scanner and not to that of the bed movement. In the prior art, such angling is generally provided so that transaxial slices are properly positioned with respect to the anatomy that is being imaged. Thus, such angling is generally between 7 and 15 degrees, since lesser changes do not generally improve visualization to a significant extent.

SUMMARY OF THE INVENTION

The present invention relates generally to the optimization, or at least the reduction, of the length of traverse of the bed while the patient is irradiated with x-rays.

An aspect of some embodiments of the invention the axis of rotation of the x-ray tube (hereinafter the "CT axis") and the axis of the bed motion are angled with respect to each other by a small amount, generally less than 2 degrees and almost always less than 5 degrees.

In some embodiments of the invention, the x-ray detector rings are angled together with the CT axis.

In modern helical CT scanners the number of slices and hence the pitch of the scan is increased. This results in a marked reduction in the number of rotations of the X-ray tube that are required. In many cases, about one rotation is sufficient. Under these circumstances, the useless exposure of regions that are not contained in a desired volumetric region of interest (VROI) can be a significant portion of the total radiation exposure of the patient. Reduction in the scan length by even a fraction of a rotation, while still imaging the desired VROI, can result in a significant overall reduction in the patient radiation exposure.

In exemplary embodiments of the invention, the angle of rotation at which the x-ray irradiation begins is adjusted to reduce the length of the traverse of the patient during which irradiation is to be performed to a minimum value.

In some embodiments of the invention, the angle between the helix axis and the axis of a cylindrical volumetric region of interest (generally the same as the patient motion axis) is set to an angle at which the central fan of the cone provides the central parallel view data necessary for the edges of the top or bottom of the cylinder, on a same rotation. The angle of starting the x-ray is optionally set so that it begins 90° of rotation before the central fan of the cone first intersects a first one of these edges. This allows the central parallel view to be generated from attenuation paths that are all from the central fan of the beam. In some situations, the end of the rotation is also at a functionally similar angle. In others, due to the length chosen, this is not possible. In some embodiments, a compromise angle, to provide minimum irradiation of the patient is used or other optimizations are used.

There is thus provided, in accordance with an embodiment of the invention, computerized tomography apparatus for reconstructing attenuation values within a volume comprising:

an x-ray source situated operative to rotate about said volume, in a rotation plane, while irradiating at least a portion of the volume;

a plurality of rows of x-ray detectors illuminated by said rotating x-ray source situated on an opposite side of the volume;

a patient support operative to move a patient through a space between the source and detectors at an angle to the normal to the rotation plane, while the x-ray source illuminates the detectors; and a controller operative to compute the angle based on at least one of a radius R of said rotation, a radius r of said volume and a helix pitch, m, defined as a distance the patient support moves during a single rotation of the x-ray source.

Optionally, the angle is more than 0.5 degrees and less than 5 degrees.

There is further provided, in accordance with an embodiment of the invention, computerized tomography apparatus for reconstructing attenuation values within a volume having a radius r, comprising:

an x-ray source situated operative to rotate about said volume at a radius R, while irradiating at least a portion of the volume;

a plurality of rows of x-ray detectors illuminated by said rotation x-ray source situated on an opposite side of the volume;

a patient support operative to move a patient through said volume at an angle to the normal to the rotation plane, while the x-ray source illuminates the detectors, such that the apparent rotation of the x-ray source at least approximately defines a helix pitch m defined as a distance the patient support moves during a single rotation of the x-ray source; and a controller operative determine a desired angle of between 0.5° and 5° and to activate the x-ray source when the angle is adjusted to the desired value.

In an embodiment of the invention, the rows of detectors are oriented such that they describe a planar surface or a portion of a cylindrical surface, said surface being perpendicular to a plane of rotation of the x-ray source.

Optionally, the angle is between 0.7 and 1.5 times arc tan $(m/2\pi R)$. Optionally, the angle is between 1 and 1.25 times arc tan $(m/2\pi R)$. Optionally, the angle is between 1 and 1.15 times arc tan $(m/2\pi R)$.

In an embodiment of the invention, the angle is within 1, 0.5 or 0.25 degrees of arc tan $(\Delta z/r)$, where $\Delta z = \beta * m/2\pi$ and $\beta = 2 \text{arc sin}(r/R)$.

In an embodiment of the invention, where the volume is a right circular cylindrical volume and including a controller that controls the start of the x-ray such that a central fan of a cone beam produced by the x-ray source provides attenuation data for a central parallel view of the end of the volume, the attenuation data being for lines parallel to the end of the volume.

In an embodiment of the invention, where the volume is a right circular cylindrical volume and including a controller that controls the start of the x-ray such that the x-ray commences at about 90° of rotation of the source prior to the first intersection of a central fan of the cone beam with the end of the volume.

Optionally, the controller shuts off x-ray at a position on the other end of the volume to be reconstructed corresponding, in mirror image to the start of x-ray position.

There is further provided, in accordance with an embodiment of the invention, a method of tomographic imaging of a cylindrical volumetric region of interest VROI, having a radius r, utilizing a CT imager, the imager comprising an x-ray source adapted to rotate in a plane about said VROI while irradiating at least a portion of the VROI, a plurality of rows of x-ray detectors illuminated by said rotation x-ray source situated on an opposite side of the VROI and a support defining an axis of the VROI, the method comprising:

moving the support and the associated VROI through the irradiated region; and tilting the plane of rotation of the x-ray source so that the axis of the VROI and the normal of the plane of rotation form an angle between 0.5° and 5°; and irradiating the VROI while it moves through the plane of rotation at said angle.

In an embodiment of the invention, the rows of detectors are oriented such that they describe a planar surface or a portion of a cylindrical surface, said surface being perpendicular to a plane of rotation of the x-ray source. Optionally, the angle is between 0.7 and 1.5 times arc tan $(m/2\pi R)$. Optionally, the angle is between 1 and 1.25 times arc tan $(m/2\pi R)$. Optionally, the angle is between 1 and 1.15 times arc tan $(m/2\pi R)$.

In an embodiment of the invention, the angle is within 1, 0.5 or 0.25 degrees of arc tan $(\Delta z/r)$, where $\Delta z = \beta * m/2\pi$ and $\beta = 2 \text{arc sin}(r/R)$.

In an embodiment of the invention, the volume is a right circular cylindrical volume and the method includes initiating the x-ray such that a central fan of a cone beam produced by the x-ray source provides-attenuation data for a central parallel view of the end of the volume, the attenuation data being for lines parallel to the end of the volume.

In an embodiment of the invention, the volume is a right circular cylindrical volume and initiating the x-ray such that the x-ray commences at about 90° of rotation of the source prior to the first intersection of a central fan of the cone beam with the end of the volume.

Optionally, the method includes shut off of the x-ray at a position on the other end of the volume to be reconstructed corresponding, in mirror image to the start of x-ray position.

BRIEF DESCRIPTION OF FIGURES

Exemplary, non-limiting embodiments of the invention are described in the following description, read in with reference to the figures attached hereto. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DESCRIPTION OF EXEMPLARY EMBODIMENTS

Figure 1:
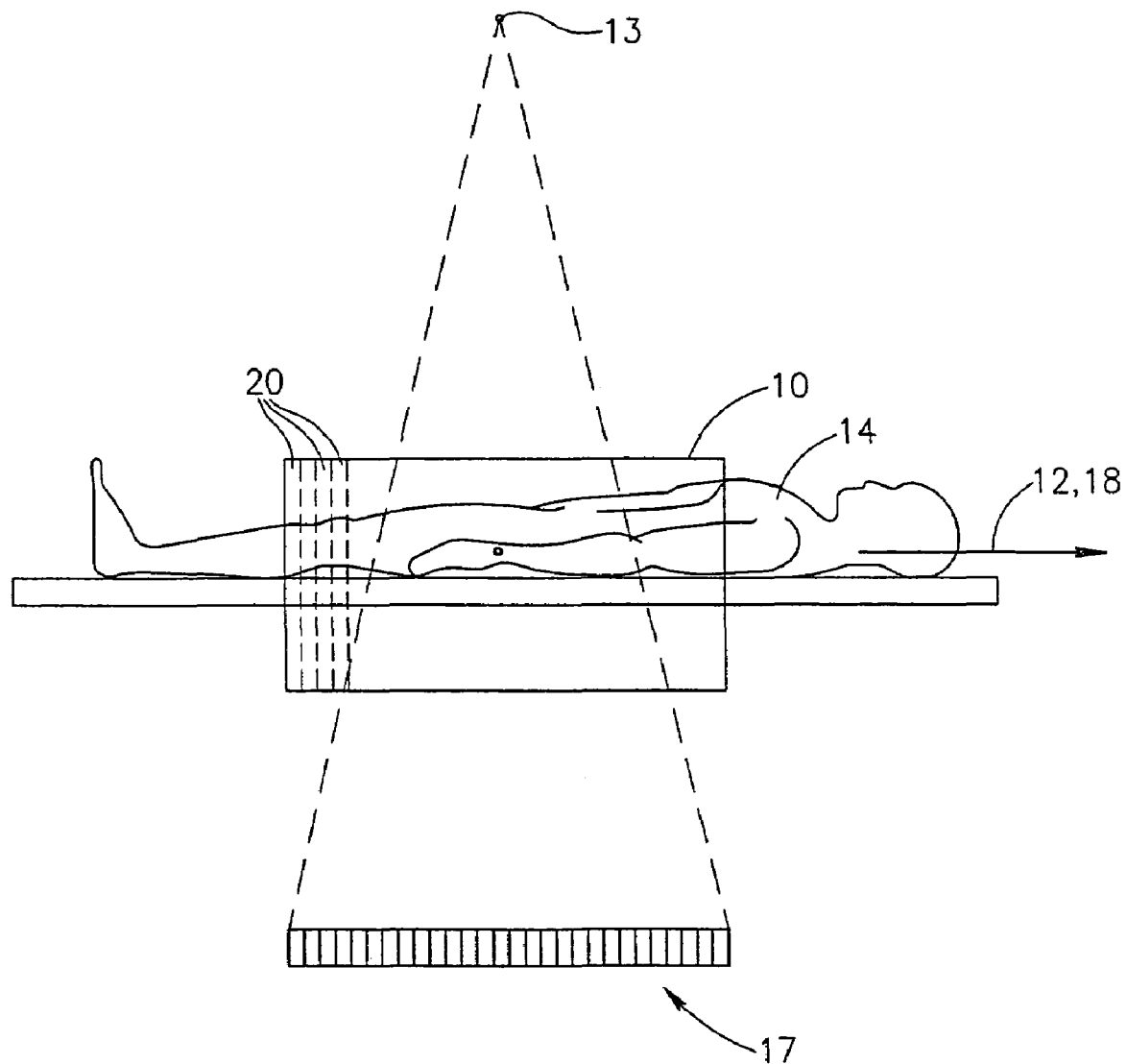
FIG. 1 shows a generalized schematic, non-limiting, view of a CT imager, according to the prior art, showing those elements necessary to the understanding of the present invention.

FIG. 1 shows a side view illustrating the geometry of a multi-slice cone beam according to the prior art. A cylindrical volumetric region of interest (VROI) 10 having a patient axis 12 is scanned by an X-ray source 13, while rotating about a rotation (CT) axis 18, which is shown as being coincident with axis 12 for the prior art system shown. A patient 14 moves in a direction 12. Marked on VROI 10 are a series of slices 20 (only a few of which are indicated), for which images are desired. In the prior art system, when transaxial slices (as shown) are to be imaged, the patient axis and the CT axis are coincident.

Figure 2:
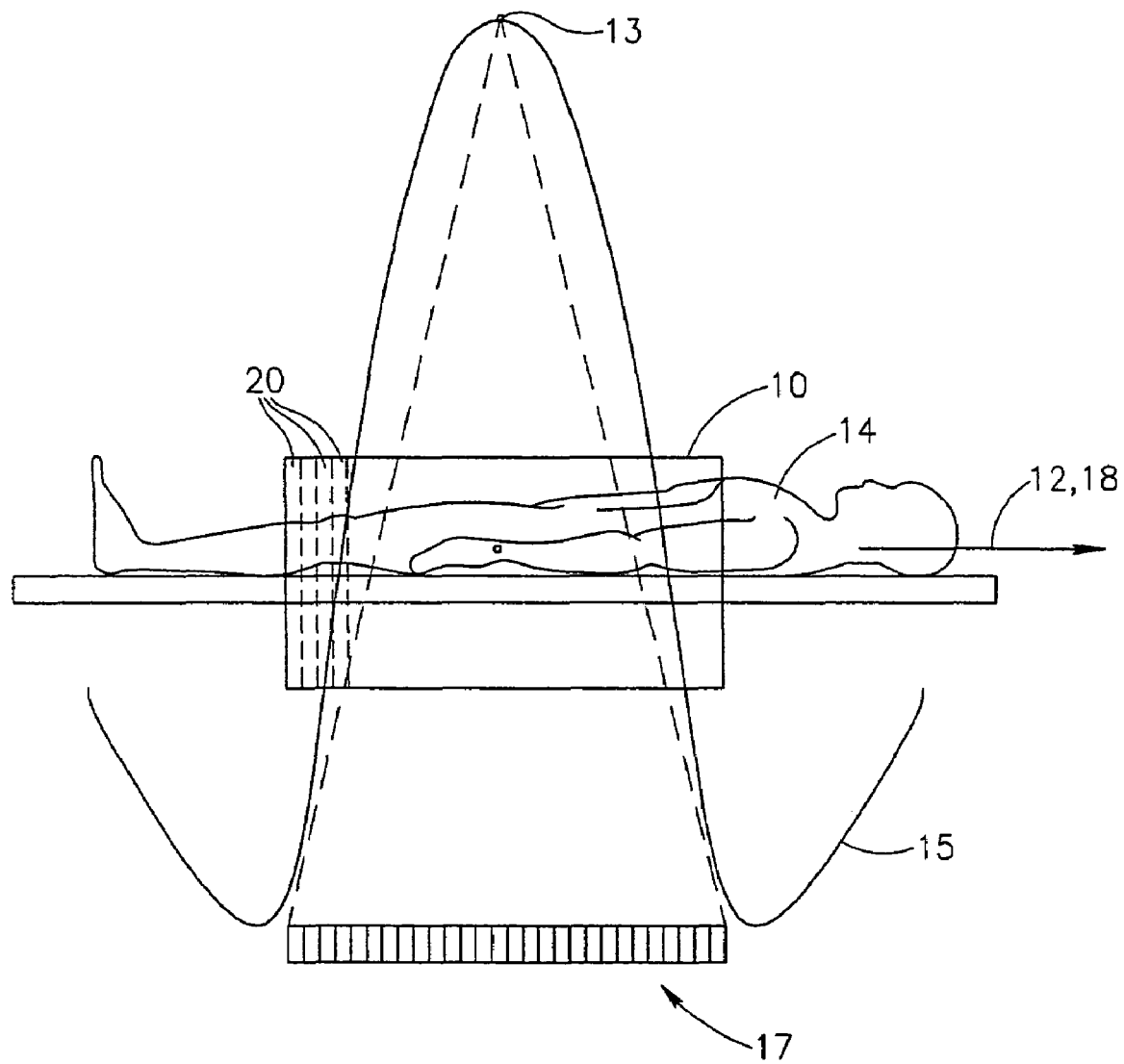
FIG. 2 shows a different presentation of a CT imager equivalent to that of FIG. 1.

For the purposes of description of the present invention, the presentation of FIG. 2, which is equivalent to that of FIG. 1, is useful. While in FIG. 1, the patient is considered to have the motion along its axis and the X-ray source is considered to have a pure rotational motion, in FIG. 2, source 13 is shown as describing a helical motion 15 and the patient is considered to be stationary. The axis of the helix is the same as the axis of rotation of the x-ray source. The two descriptions are, of course completely equivalent.

Figure 3:
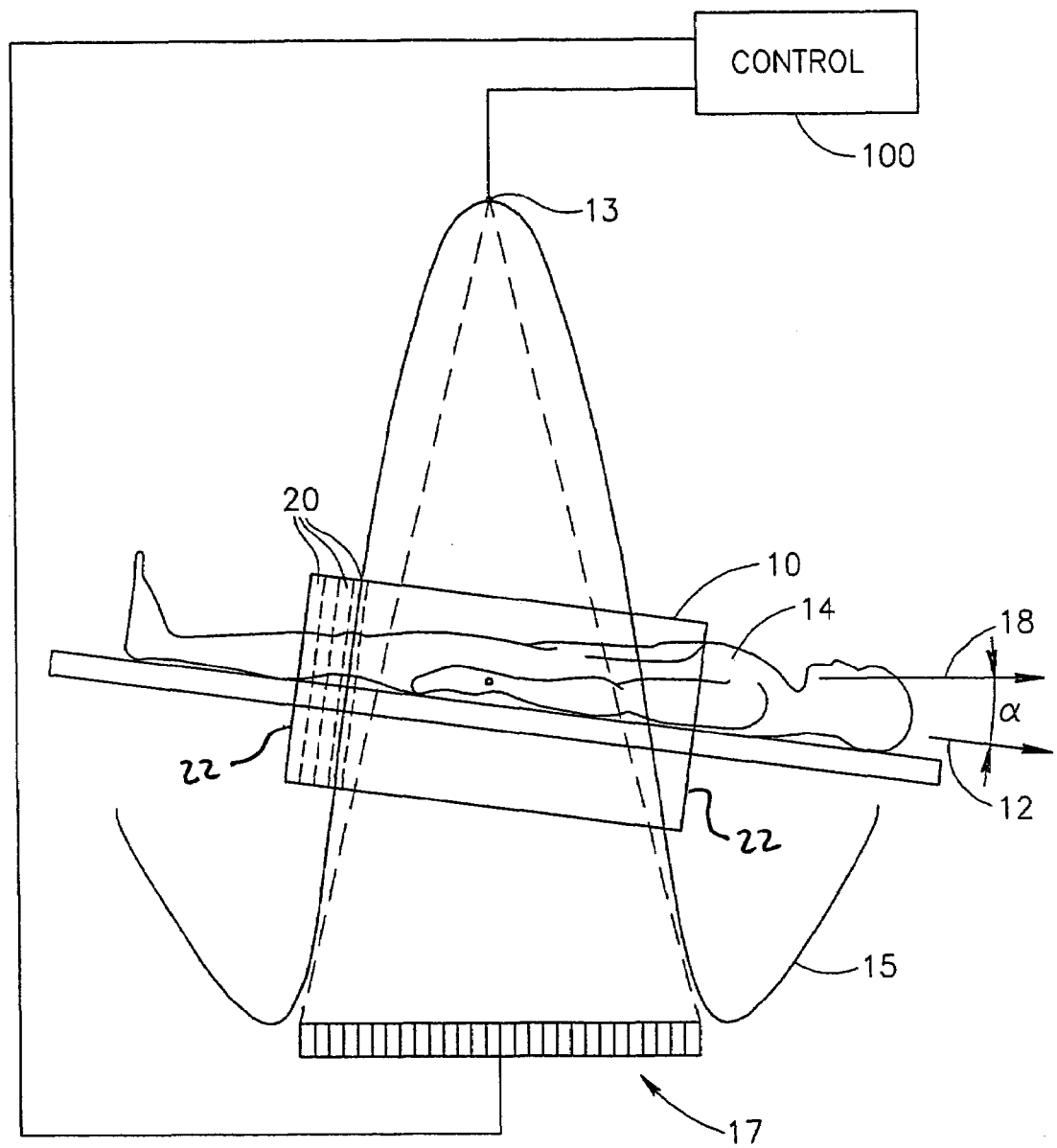
FIG. 3 shows a configuration, presented in the style of FIG. 2, of a angular tilt between the axis of a patient and an axis of a rotation path (helix) formed by the rotation of the x-ray source.

FIG. 3, which corresponds to FIG. 2 shows a side view of the same VROI 10 and the same desired transaxial (with respect to patient axis 12) slices 20. However, unlike the situation in prior art FIG. 1, patient axis 12 and CT rotation axis 18 are offset by an angle .alpha.. This angle is preferably chosen to minimize the amount of radiation to the patient by minimizing the number of rotations of the x-ray tube about the patient. Although the angular offset is shown as being about 12°, the actual offset in various embodiments of the invention, is usually much smaller. It should also be noted that in FIG. 3, the patient is shown as being tilted. However, in practice it is generally more convenient to tilt the plane of the gantry, generally tilting both the circle of rotation of the x-ray source and the detectors 17 by a same angle .alpha.. Since many modern CT imagers have the facility for such tilting, the practice of the present invention generally does not require the use of special equipment. A controller 100, controls the x-ray source, and received data signals from the detectors 17, as in conventional systems. It also determines an angle of tilt, as described below and controls the tilt of the gantry (or the table) to provide the tilt angle .alpha.. In general the term controller is used to include the apparatus and software necessary for computing and displaying tomographic images based on the determined attenuation values.

While the path of the x-ray source is shown as a helix, this is true only with respect to a moving reference, as described below. While the following explanation is not strictly speaking, required for an understanding of the invention, it is included to further orient the reader.

For the purpose of formulating the orientation of the VROI with respect to the helical path, it is convenient to chose a Cartesian system of coordinates (SOC) that has a z-axis with the same direction as the rotation axis of the tilted gantry. The origin of the SOC is fixed to the center of the cylinder, i.e., the origin of the SOC moves with the patient. This is the same movement that was used to generate the helix shown in FIG. 2. In the embodiment of FIGS. 1 and 2, the movement is perpendicular to the rotation plane of the rotation of the x-ray source, such that in the SOC, the movement of the x-ray source is a true helix with a fixed axis.

In the embodiment of FIG. 3, the origin of the SOC does not move in the direction normal to the rotation plane, so the analysis is somewhat more complex. In the SOC of FIG. 3, the outside surface of the VROI is defined parametrically with respect to φ and h, as:

$$x_c = r^*\cos(\phi)^*\cos(\alpha) + h^*\sin(\alpha) \quad (1)$$

$$y_c = r^*\sin(\phi) \text{ and} \quad (2)$$

$$z_c = r^*\cos(\phi)^*\sin(\alpha) + h^*\cos(\alpha) \quad (3)$$

where r is the radius of the cylinder of the VROI, $\alpha$ is the gantry tilt angle, $\phi$ is a parameter that varies between 0 and $2\pi$ and h is a parameter that varies between $-H/2$ and $+H/2$, where H is the height of the cylinder.

In the coordinate system indicated above, the helical path of the X-ray source is given by:

$$x_s = z_s^*\tan(\alpha) + R^*\cos(\theta_o + 2\pi^*z_s/(m^*\cos(\alpha))) \text{ and} \quad (4)$$

$$y_s = R^*\sin(\theta_o + 2\pi^*z_s/(m^*\cos(\alpha))). \quad (5)$$

where R is the radius of the X-ray source rotation around the gantry iso-center, m is the helical pitch and $\theta_o$ is a phase of the helical path. The term $z_s^*\tan(\alpha)$ in equation (4) reflects the fact that for a tilted gantry (with the origin of coordinated fixed in the center of the VROI), the path of the x-ray source is a helical path with respect to a point that moves. While the direction of the z-axis is the same as the direction of the helix axis, the position of the axis in the x-y plane moves with respect to the center of the helix. For simplicity, we assume that the tilt is in the x-z plane.

It should be understood that the above equations 4 and 5 highlight that there are two degrees of freedom in the tilt, namely the tilt angle $\alpha$ and the phase of the helix $\theta_o$. The dose can be reduced by properly choosing the angle, with further optimization being based on a choice of the helix phase.

It is noted that the angle of the helix with respect to VROI 10 is such that the helix path is parallel to one and preferably to both of end faces 22 of VROI 10 (parallel to one end, in the embodiment shown), as the x-ray tube passes the end faces. This congruency and the reasons why it is desirable are explained with the aid of FIG. 4.

Figure 4:
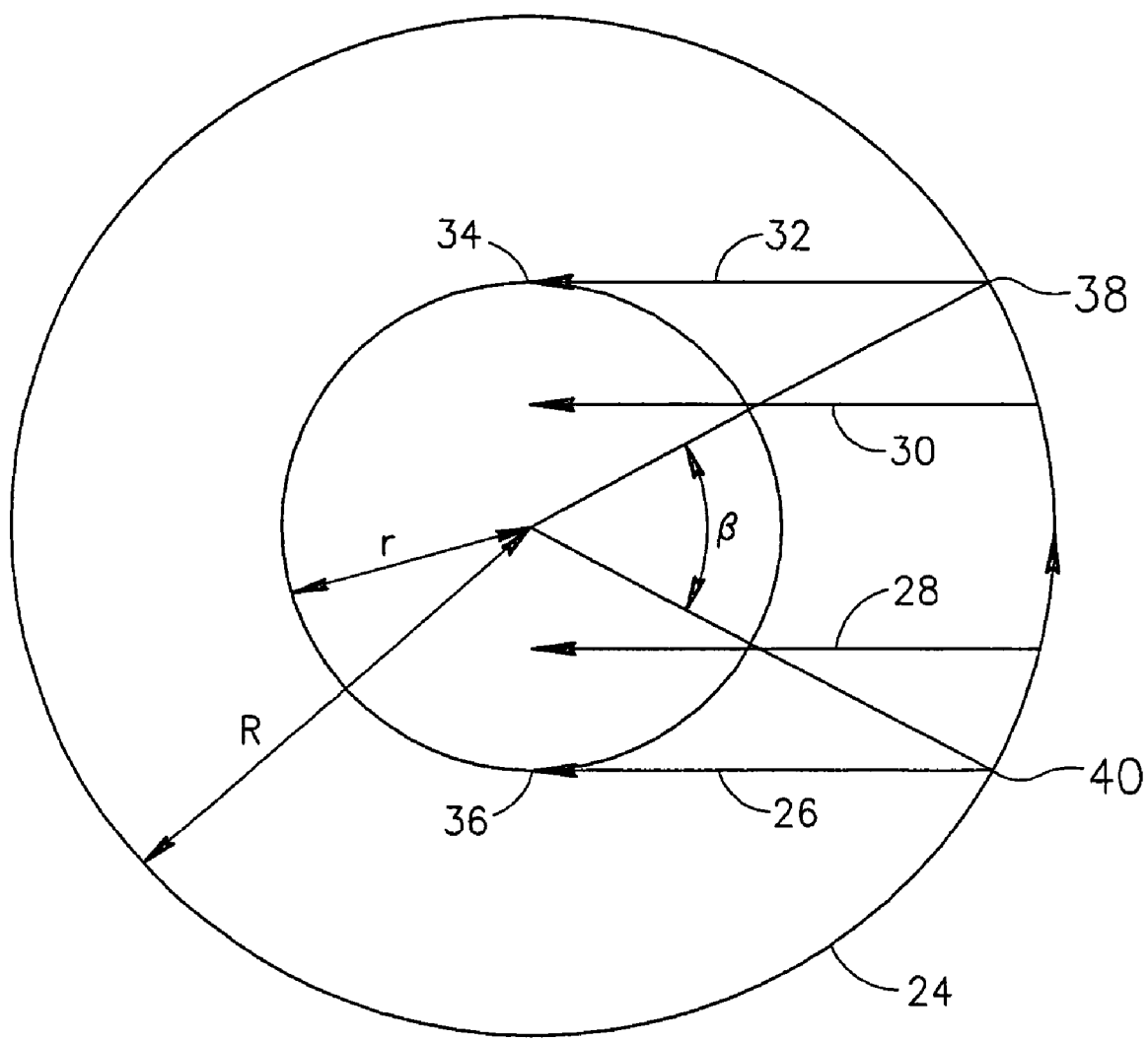
FIG. 4 shows an end view of a VROI together with a circle describing the rotation of the x-ray source.

FIG. 4, shows an end view of VROI 10, together with a circle 24, representing the rotation path of the x-ray source. Also shown are a plurality of beams 26, 28, 30 and 32, corresponding to a some of the group of beam paths of CT "view" for reconstruction of an image of an end slice of the VROI. This group of beam paths is provided by rebinning of the fan/cone beam data to parallel views, by any of the many methods known in the art.

In accordance with an embodiment of the invention, one of the parallel views necessary for reconstructing the slice is derived during a single partial rotation of angle $\beta$, as indicated on the drawing. Optionally, each of the elements in the group making up a particular view, are provided from the same fan of the cone beam. By simple geometry, it can be seen that $\beta = 2^*\arcsin(r/R)$.

In FIG. 4, 34 and 36 represent two pixels at the extreme of the reconstruction circle of the particular view (i.e., the VROI) and 38 and 40 correspond to the positions of the x-ray source when these beams are acquired. It is clear that in order for the same fan beam to be used for all the elements of the group, the x-ray source should move ($\Delta z$), during a rotation $\beta$, by a distance given as:

$$\Delta z = \beta^* m/(2\pi), \quad (6)$$

where m is the movement of the bed during one gantry rotation (i.e., the pitch of the helix). Movement by this amount will provide for the same fan to remain aligned with the slice during the rotation through the angle $\beta$.

In order to achieve this condition, patient axis 12 and helix axis 18 should be tilted by an angle:

$$\alpha = arc\ \tan(\Delta z/2\pi), \quad (7)$$

which is approximately equal to the helix angle, for values of r/R of less than about 0.5 and somewhat larger than the helix angle for larger values of r/R. In all practical cases, the above analysis yields a value of a within 15% or 25% of the helix angle. While the calculated value gives optimum results, values between 0.7 and 1.5 times the helix angle also give a substantial reduction in the radiation dose. More preferably, a is between the helix angle and 1.25 times the helix angle. Optimally, it is substantially equal to the angle defined by the above equations (i.e., within 0.25, 0.5 or 1 degrees)

For example, for R=285 mm, and m=100 (for a multi-slice scanner), a is between approximately 3.3° and 3.7°, for a range of r between 125 and 250. This angle is, of course dependent on r, R and m and will vary depending on the value of these variables. It is believed that in practical situations a will be between 0.5° and 5°. For most structures it will be between 1° and 4°. For some structures it will be between 2° and 3°. In accordance with the above analysis, the total rotation required to produce all of the views for the slice is just 180°+β. The above analysis describes the optimization of the acquisition of the data for reconstructing one of the end slices.

The above analysis describes an optimization procedure for a slice at one end of VROI 10. Optimally, the amount of radiation is reduced by a maximum amount if the same conditions apply at the other end of the VROI. This occurs when the length of the VROI is an integer multiple of the pitch.

Under these circumstances, the helical path can be reduced by 2*arc sin(r/R). For example, if r=0.667R, the decrease is over 83°. Where the length of the VROI is equal to a small multiple of the pitch, the reduction in radiation can be quite substantial. This gives over 10% decrease in radiation dose, when a large helix pitch is used. When a smaller helix pitch is used, so that several rotations of the x-ray source are required, or where r/R is smaller, the improvement will be smaller.

In order to acquire all of the attenuation values for the central view from the central fan, the x-ray should be on just as the fan first intersects the end surface. However, since this is the central view, the earlier views are acquired earlier. This means that the x-ray is preferably turned on 90° of rotation of the x-ray source before this first intersection. When the length of the VROI is equal to an integer number of pitches, this will result optimization at both ends of the VROI. Utilizing the Cartesian system described above, the phase angle of the helix at which the scan commences is optimally is:

$$\theta_o = 2\pi((\tfrac{1}{2}H\cos(\alpha)) + R\sin(\alpha))/m\cos(\alpha). \quad (8)$$

For other lengths, a compromise starting angle can be chosen or only one end is optimized. Alternatively, the pitch is adjusted to optimize the radiation, consistent with image quality requirements. Further alternatively, under some circumstances the angle is made somewhat different than the calculated a. Generally, some combination of these variations can be used. The exact values that give the lowest dosage will depend, to some extent on the particular geometry of the system and the length of the VROI, such that a general formulation may not be possible. However, utilizing the general basis as described herein, the angle α for any optimization are expected to be 25% of the value calculated above.

The above embodiment describes the application of the present invention to system in which parallel views are generated by rebinning the data into parallel views and reconstructing the image from the parallel views. As such it is directly applicable to wide range of cone beam reconstruction algorithms, such as the above-mentioned paper by Kachelrieβ, et al, and M. "A 3D cone beam reconstruction for circular trajectories," by M. Grass, et al., Phys. Med. Biol., Vol. 45, P329 (2000). However, the present invention is also applicable to other reconstruction methods, for example three dimensional reconstruction methods such as those described in "Exact Radon Rebinning Algorithm for the Long Object in Helical Cone Beam CT", by Schaller, et al, IEEE Trans. Med. Imag. Vol. 19, p. 361 (2000) and "Quasi-exact filtered backprojection algorithm for long-object problem in helical cone-beam Tomography," by Kudo, et al., IEEE Trans. Med. Imag. Vol. 19, p. 902 (2000). The disclosures of all of these papers are incorporated herein by reference. Furthermore, in the above analysis the effect of the use of views having a path that is not parallel to the plane is not dealt with. However, such problems are dealt with in substantially all cone beam reconstruction algorithms.

Furthermore, the present invention has been described using non-limiting detailed descriptions of exemplary embodiments thereof that are provided by way of example and that are not intended to limit the scope of the invention. Variations of embodiments of the invention, including combinations of features from the various embodiments will occur to persons of the art. For example, both third and fourth generation CT scanners can be used as can multiple focal spot systems (for higher resolution) and systems in which a ring x-ray source in which a beam impinging a ring target (the x-ray source) travels around the patient is used rather than a rotation x-ray tube. Furthermore, while the invention has been described for the imaging of a patient, it is well known that CT imaging can also be used to image the interior of other objects such as castings and machined parts. The scope of the invention is thus limited only by the scope of the claims. Furthermore, to avoid any question regarding the scope of the claims, where the terms "comprise," "comprising," "include," "including" or the like are used in the claims, they mean "including but not necessarily limited to".

The invention claimed is:

1. Computerized tomography apparatus for reconstructing attenuation values within a volume comprising: an x-ray source situated operative to rotate about said volume, in a rotation plane, while irradiating at least a portion of the volume; a plurality of rows of x-ray detectors illuminated by said rotating x-ray source situated on an opposite side of the volume; a patient support operative to move a patient through a space between the source and detectors at an angle to the normal to the rotation plane, while the x-ray source illuminates the detectors; and a controller operative to compute the angle based on at least one of a radius R of said rotation, a radius r of said volume and a helix pitch, m, defined as a distance the patient support moves during a single rotation of the x-ray source.

2. Apparatus according to claim 1 wherein the angle is more than 0.5 degrees and less than 5 degrees.

3. Apparatus according to claim 1 wherein the rows of detectors are oriented such that they describe a planar surface or a portion of a cylindrical surface, said surface being perpendicular to a plane of rotation of the x-ray source.

4. Apparatus according to claim 1 wherein the angle is between 0.7 and 1.5 times arctan $(m/2\pi R)$.

5. Apparatus according to claim 4 wherein the angle is between 1 and 1.25 times arctan $(m/2\pi R)$.

6. Apparatus according to claim 4 wherein the angle is between 1 and 1.15 times arctan $(m/2\pi R)$.

7. Apparatus according to claim 1 wherein the angle is within 1 degree of arctan $(z/r)$, where $z=\beta*m/2\pi$ and $\beta=2\arcsin(r/R)$.

8. Apparatus according to claim 7 wherein the angle is within 0.5 degrees of arctan$(z/r)$.

9. Apparatus according to claim 7 wherein the angle is within 0.25 degrees of arctan $(z/r)$.

10. Apparatus according to claim 1 wherein the volume is a right circular cylindrical volume and including a controller that controls the start of the x-ray such that a central fan of a cone beam produced by the x-ray source provides attenuation data for a central parallel view of the end of the volume, the attenuation data being for lines parallel to the end of the volume.

11. Apparatus according to claim 10 wherein the controller shuts off x-ray at a position on the other end of the volume to be reconstructed corresponding, in mirror image to the start of x-ray position.

12. Apparatus according to claim 1 wherein the volume is a right circular cylindrical volume and including a controller that controls the start of the K-ray such that the x-ray commences at about 90° of rotation of the source prior to the first intersection of a central fan of the cone beam with the end of the volume.

* * * * *